(12) United States Patent
Mace

(10) Patent No.: US 8,337,201 B1
(45) Date of Patent: Dec. 25, 2012

(54) SELF-POSITIONING DENTAL LIGHT FILTERING DEVICE

(76) Inventor: James Gordon Mace, Washington, MO (US)

( * ) Notice: Subject to any disclaimer, the term of this patent is extended or adjusted under 35 U.S.C. 154(b) by 0 days.

(21) Appl. No.: 13/545,044

(22) Filed: Jul. 10, 2012

Related U.S. Application Data

(60) Provisional application No. 61/572,089, filed on Jul. 11, 2011.

(51) Int. Cl.
*A61C 1/00* (2006.01)

(52) U.S. Cl. .......................................................... 433/29

(58) Field of Classification Search .................... 433/29; 2/1, 7, 10–17
See application file for complete search history.

(56) References Cited

U.S. PATENT DOCUMENTS

| | | |
|---|---|---|
| 1,178,420 A | 4/1916 | Sibley |
| 2,054,230 A | 9/1936 | Patterson |
| 3,154,253 A | 10/1964 | Guth |
| 4,214,393 A | 7/1980 | Long |
| 4,392,188 A | 7/1983 | Norris |
| 4,878,156 A | 10/1989 | Hallings et al. |
| 5,288,231 A | 2/1994 | Kuehn et al. |
| 5,537,205 A | 7/1996 | Costa et al. |
| 5,749,724 A | 5/1998 | Cheng |
| 5,759,032 A | 6/1998 | Bartel |
| 6,011,219 A | 1/2000 | Casmero |
| 6,155,823 A | 12/2000 | Nagel |
| 6,325,623 B1 | 12/2001 | Melnyk et al. |
| 6,345,982 B1 | 2/2002 | Meyer |
| 6,384,420 B1 | 5/2002 | Doriguzzi Bozzo |
| 7,658,013 B2 | 2/2010 | Tung |
| 2003/0008260 A1 | 1/2003 | Wang et al. |
| 2004/0029069 A1 | 2/2004 | Gill et al. |
| 2006/0252005 A1 | 11/2006 | Feinbloom et al. |
| 2007/0134616 A1 | 6/2007 | Gill et al. |
| 2009/0176186 A1 | 7/2009 | Swift |
| 2010/0273123 A1 | 10/2010 | Mecher |
| 2011/0185465 A1 | 8/2011 | Prinkey |
| 2011/0236851 A1 | 9/2011 | Müller et al. |
| 2011/0240543 A1 | 10/2011 | Kozey |
| 2012/0070798 A1 | 3/2012 | Teitelbaum |

FOREIGN PATENT DOCUMENTS

WO 2008120002 A1 10/2008

OTHER PUBLICATIONS

Henry Schein Dental 2012 Merchandise Catalog, pp. 347, 348, 349, 350, 353 and 354.

*Primary Examiner* — Cris L Rodriguez
*Assistant Examiner* — Mirayda A Aponte
(74) *Attorney, Agent, or Firm* — Senniger Powers LLP

(57) ABSTRACT

A self-positioning dental light filtering device is disclosed. The filtering device includes a transparent filter member for blocking optically harmful light emitted from a tip of a dental curing device, and a rotational bearing having an inner component defining an opening for receiving the tip. A retaining device holds the tip substantially centered inside the rotational bearing and substantially rotationally stationary relative to the inner component of the rotational bearing. A counterweight below the rotational bearing causes the filter member to remain in an upright position above the tip when the tip of the curing device and/or curing device itself is rotated.

17 Claims, 5 Drawing Sheets

SELF-POSITIONING DENTAL LIGHT FILTERING DEVICE

CROSS-REFERENCE TO RELATED APPLICATION

This application is a non-provisional patent application and claims priority from U.S. Provisional Patent Application Ser. No. 61/572,089, filed Jul. 11, 2011, which is incorporated herein by reference.

FIELD OF THE INVENTION

The present invention generally relates to dental equipment, and more particularly to dental equipment used for eye protection.

BACKGROUND OF THE INVENTION

Various implements have been employed in dentistry to shield the eyes of the dentist and other care providers from the optically harmful light emitted from dental curing devices. The most commonly used implements are described below.

One implement comprises a handheld filtering member that is held over the patient's mouth while the composite is cured. This is disadvantageous in several ways. First, the time taken to reach for the filtering member and hold it in place compromises efficiency since the dental assistant could be performing other duties while the dentist is curing. Also, the filtering member can sometimes be forgotten and not used, leaving the care provider's eyes vulnerable to the optically harmful light. Furthermore, the filtering members are typically large and cumbersome to store and use.

Another implement comprises a cone that is placed over the tip of the curing device. However, the cone can interfere with placement of the tip in the correct position, can push matrix systems (which are sometimes precariously placed) out of their correct positions, and allows the optically harmful light to leak out of the perimeter of the cone.

Still another implement comprises a light filtering disc that fits over the tip of the dental cure light, rests near the base of the tip by the light itself, and is secured to the tip by a grommet or some other retentive feature. This filtering disc stays outside of the patient's mouth. The disadvantage of this type of tool is that it continually needs to be adjusted to get it into the right position as the curing light is maneuvered around the mouth. This requires an extra step for the operator or the operator is forced to lean into a field of view that allows him/her to see through the filtering disc. Furthermore, when attempting to cure teeth in the very back of the mouth, this type of filtering disc can interfere with tip placement by pressing against the face of the patient and need to be adjusted to allow proper tip placement.

In summary, all of these implements have drawbacks and are difficult to use. Some clinicians choose simply not to use a filtering device because no great options are on the market. The care providers are therefore at risk from the optically harmful light. Most of these clinicians attempt to place the tip in position and look away from the light while curing. This leads to inaccuracies in tip placement which sometimes require another cure in the correct position and/or short exposures to harmful light if the curing begins prior to looking away. Thus an opportunity and need exists in the marketplace for an improved design that overcomes many of the shortfalls of the aforementioned devices and affords dental care providers with an enhanced level of convenience and protection when using dental curing lights.

SUMMARY

This invention is directed to a self-positioning dental light filtering device. In one embodiment, the light filtering device comprises a transparent filter member for blocking optically harmful light emitted from a tip of a dental curing device, and a support for supporting the filter member in an upright position above the tip of the curing device. The filtering device also includes a rotational bearing having concentric outer and inner components rotatable relative to one another about an axis of rotation. The outer component is immovable relative to the support and the inner component defines an opening for receiving the tip or other component of the dental curing device. A retaining device is provided for holding the tip or other component of the dental curing device substantially centered inside the rotational bearing and substantially rotationally stationary relative to the inner component of the rotational bearing when the tip or other component is received in the opening. A counterweight below the rotational bearing causes the filter member to remain in its upright position when the tip of the curing device and/or curing device itself is rotated about said axis of rotation.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
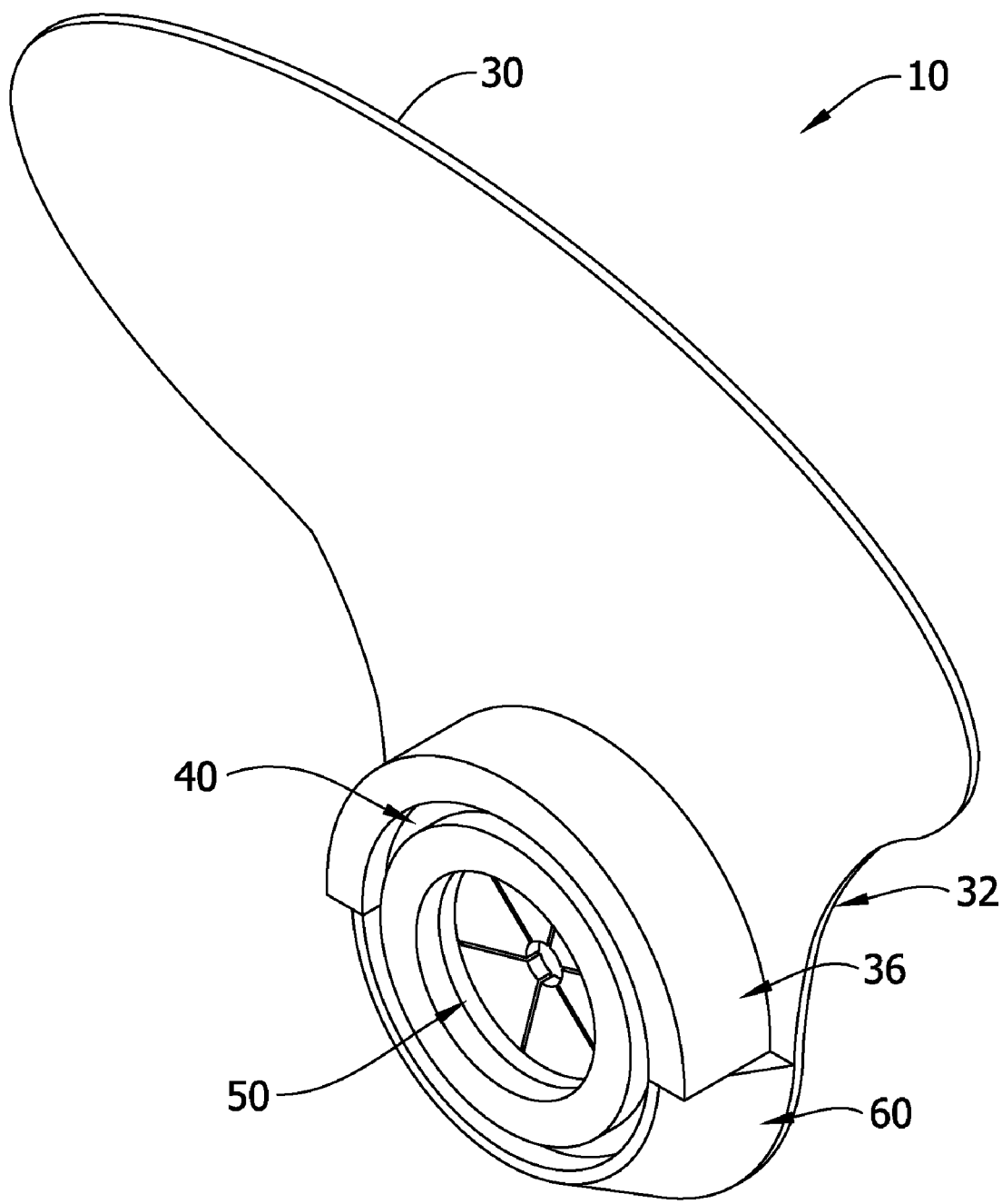
FIG. 1 is a perspective of a self-positioning dental light filtering device of this invention.

Referring now to the drawings, FIG. 1 illustrates one embodiment of a self-positioning dental light filtering device of this invention, generally designated 10. The light filtering device 10 is configured to be mounted on the tip or other component of a dental curing device for blocking optically harmful light emitted from the tip of the device. A conventional dental curing device, generally designated 20, is depicted in phantom lines in FIG. 2. The curing device has a body 22 formed as a handle to be gripped by the care provider (e.g., dentist), and an elongate tip 24 extending forward from the body. The body 22 is equipped with a light-emitting device 26, such as an LED, that emits a curing light 28 through the tip 24, as will be understood by those skilled in the field of dentistry. Typically, the tip 24 can be rotated (manually) relative to the body 22 of the curing device 20 about the longitudinal axis 29 of the tip. The curing device 20 forms no part of this invention and will not be described in further detail.

The light filtering device 10 comprises a transparent filter member 30 of a color, tint or material for blocking optically harmful light 28 emitted from the tip 24 of the dental curing device 20, and a support, generally designated 32, for supporting the filter member in an upright position above the tip 24 of the curing device 20. The light filtering device 10 also comprises a bearing mount, generally designated 36, affixed to the support 32. The bearing mount 36 supports a rotational bearing, generally designated 40, having concentric outer and inner components 42, 44 (FIG. 4), which are rotatable relative to one another about an axis of rotation 46. The outer component 42 is immovably affixed to the bearing mount 36. The inner component 44 defines an opening 38 (FIG. 5) concentric with the axis of rotation 46 for receiving the tip 24 of the curing device 20. A retaining device, generally designated 50, is provided in the opening 38 for holding the tip 24 of the curing device 20 substantially centered with the rotational bearing 40 (i.e., concentric with the axis of rotation 46 and also concentric with the longitudinal axis 29 of the tip) and substantially rotationally stationary relative to the inner component 44 of the rotational bearing 40 when the tip is received in the opening 38. A counterweight, generally designated 60, located below the rotational bearing 40 causes the filter member 30 to remain in its upright position when the tip 24 of the curing device 20 or the curing device 20 is rotated (by the care provider) about the axis of rotation 29. The components of the light filtering device 10 are described in more detail below.

The filter member 30 illustrated in the drawings is generally oval in shape, but it may have other shapes (e.g., circular, rectangular, polygonal) without departing from the scope of this invention. The filter member is of a material suitable for blocking harmful curing light 28 emitted by the curing device 20, which curing light typically is a blue light having a wavelength in the range of 450-500 nm. By way of example but not limitation, the filter member 30 may be of cell-cast acrylic. This type of acrylic is resistant to chemicals and has the desirable property of being transparent to allow optical clarity. One suitable color, amber 2422, is commonly available in the industry and is suitable for filtering the curing light 28 so that it is safe for viewing.

The oval shape of the filter member 30 allows for a small connection to the bearing and a larger viewing section in the superior position for eye protection. Desirably, the filter member 30 is of relatively thin sheet material (e.g., 1/32 in. sheet material, referred to the industry as 0.030 in. sheet). The relatively thin material is desirable to minimize the weight of the filter member 30 and offsetting counterweight 60.

Figure 4:
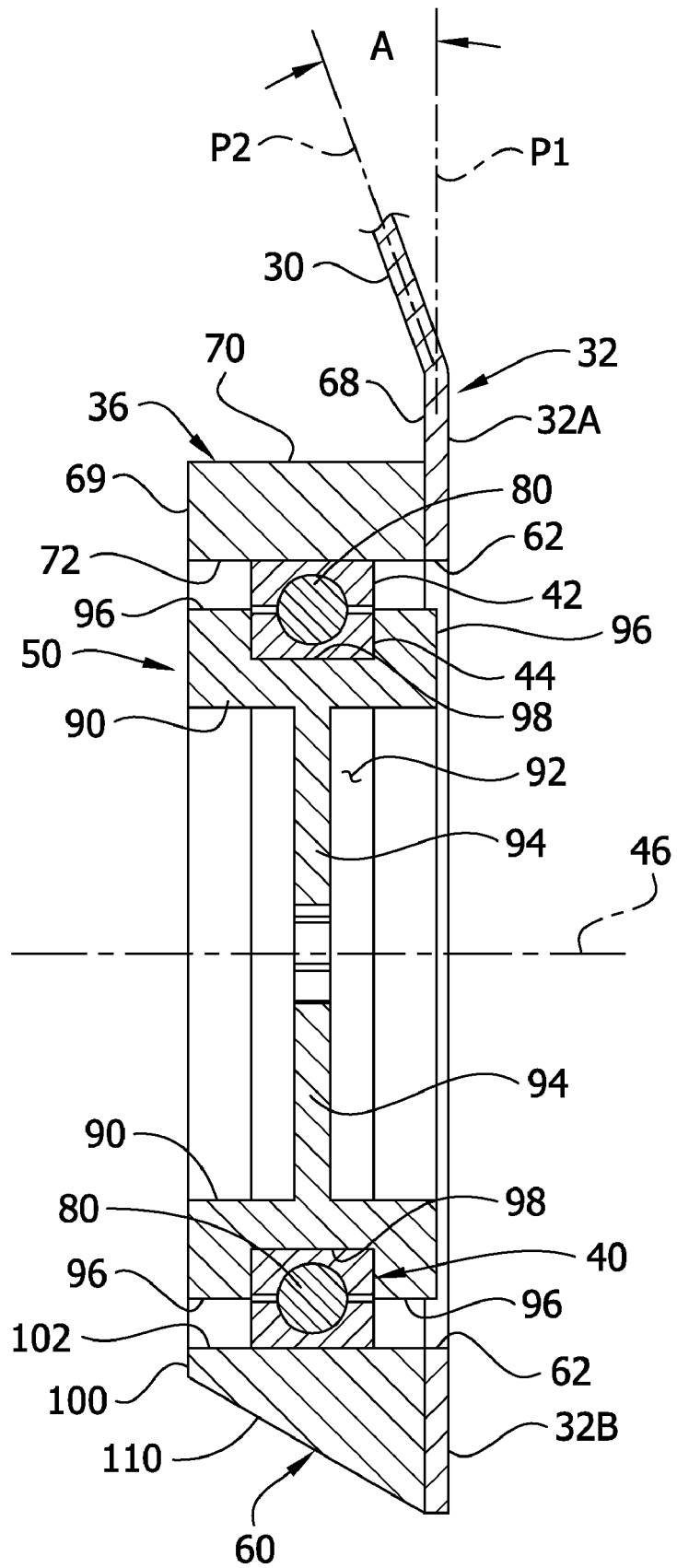
FIG. 4 is an enlarged vertical section taken in the plane of 4-4 of FIG. 3.

Referring to FIG. 4, the support 32 has an upper generally planar section 32A disposed above the rotational bearing 40 and a lower generally co-planar section 32B disposed below the rotational bearing. The upper and lower sections 32A, 32B lie in a first plane P1 generally perpendicular to the axis of rotation 46 and define a circular opening 62 that is generally concentric with the opening 38 in the rotational bearing 40 and about the same size as that opening. The filter member 30 extends from the support 32 and lies in a second plane P2 oriented at an angle A relative to the first plane P1. Desirably, this angle A is in the range of plus or minus 0-60 degrees, and even more desirably in the range of plus or minus 0-20 degrees. In one embodiment, the support 32 and filter member 30 are integrally formed as one piece from the same material (e.g., cell-cast acrylic), but they may be formed as separate pieces of the same or different material and then attached to one another.

The support 32 and/or filter member 30 can have configurations other than those described above without departing from the scope of this invention.

Figure 5:
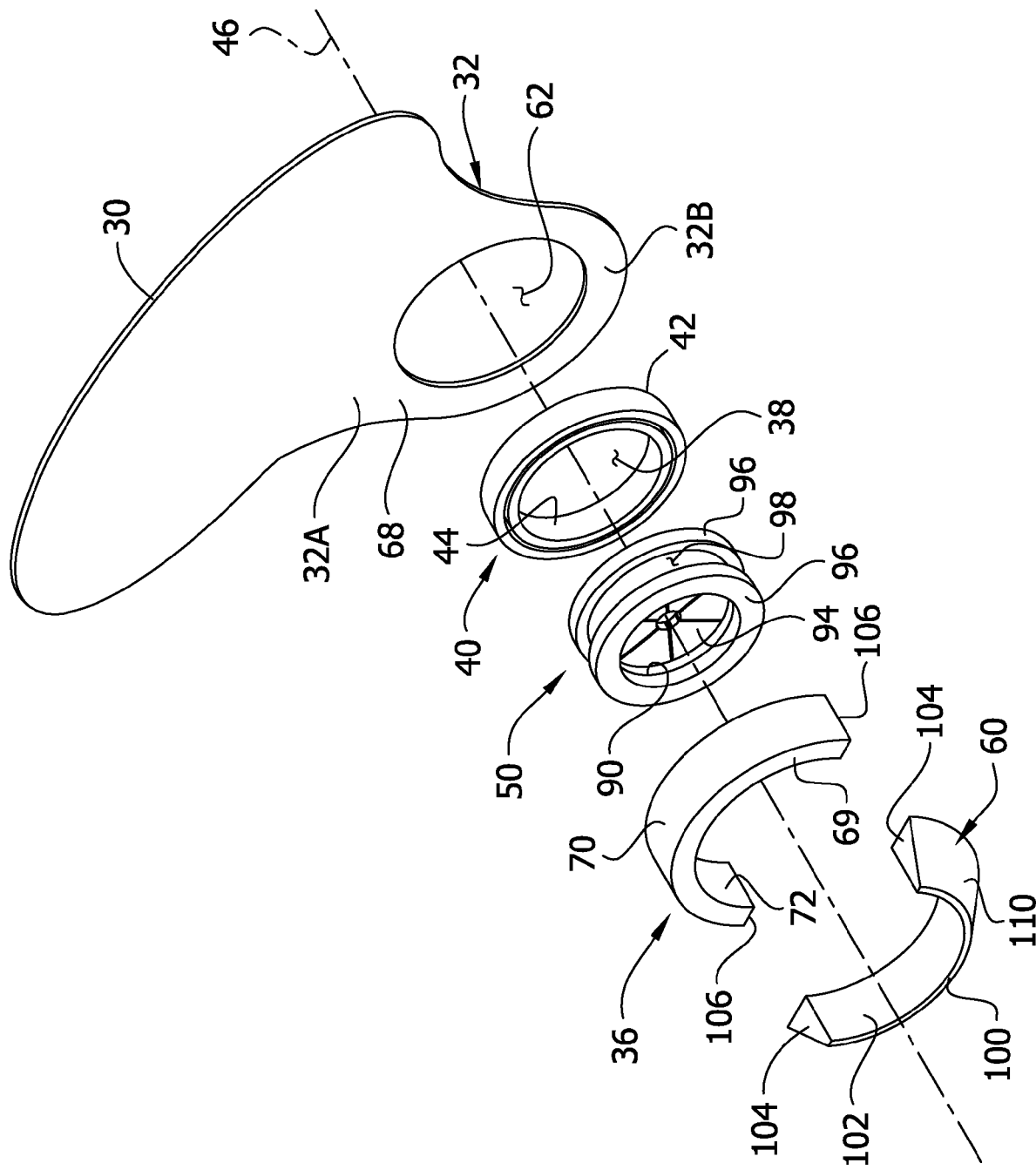
FIG. 5 is an exploded assembly view of the light filtering device showing various components.

Referring to FIGS. 4 and 5, the bearing mount 36 comprises a curved member 69 immovably affixed to one face 68 of the upper section 32A of the support 32 and at least partially surrounding the outer component 42 of the rotational bearing. The curved member 69 has an upper surface 70 and a curved (e.g., semi-circular) lower surface 72 closely conforming to the curvature of the outer component 42 of the rotational bearing. At least the lower surface 72 and desirably both the upper and lower surfaces 70, 72 are generally concentric with the axis of rotation 46. By way of example, the curved member 69 may be a part-circular section (e.g., semi-circular section) of acrylic tubing adhered to the support 32. The bearing mount 36 may have other configurations without departing from the scope of this invention.

In the illustrated embodiment, the rotational bearing 40 is a thin-section rolling-element bearing, such as a bearing commercially available from, for example, Alpine Bearing Co. in Allston, Mass. The outer component 42 of the bearing comprises an annular outer race, also designated 42, immovably affixed (e.g., adhered) to the curved lower surface 72 of the bearing mount 36 and to the counterweight 60. The inner component 44 of the bearing comprises an annular inner race, also designated 44, having an inside diameter defining the tip opening 38. Balls or other roller elements 80 positioned between the two races 42, 44 allow relative rotation between the inner and outer bearing components. The inside diameter (ID) of the inner annular race 44 is relatively close to the outside diameter (OD) of the outer annular race 42. By way of example, the difference between the ID and OD may be about 0.125 in. or less. A thin-section rotational bearing allows the bearing to be relatively small yet have a relatively large opening sufficient to accommodate the retaining device 50 and curing devices having tips of varying diameter. The bearing 40 is lubed with an oil of a viscosity that provides the right amount of movement without being too stiff. Other types of rotational bearings may also be used.

Figure 3:
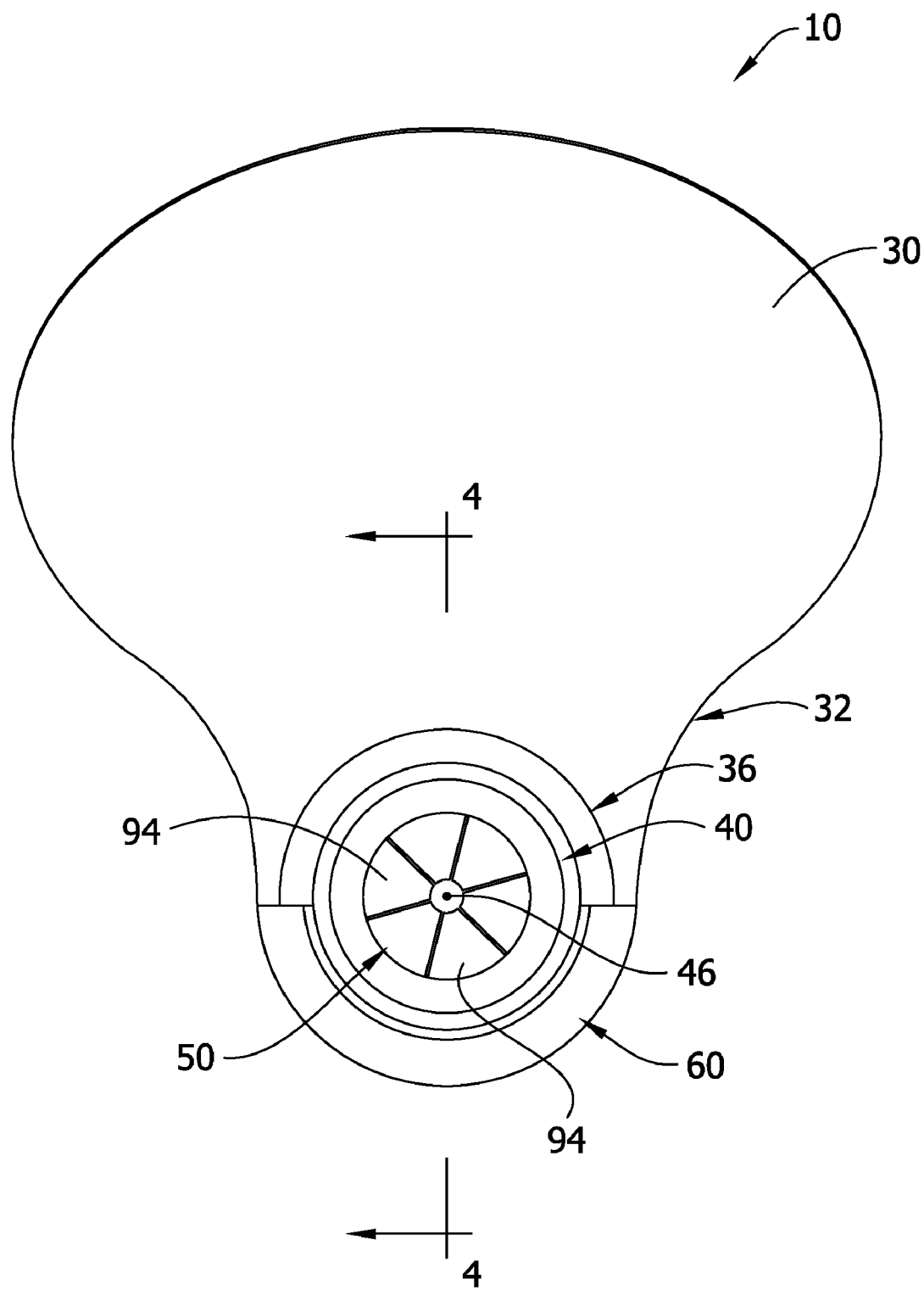
FIG. 3 is a front elevation of the light filtering device of FIG. 1.

Referring to FIGS. 3-5, the retaining device 50 comprises a ring 90 fitted inside the tip opening 38 defined by the inner component 44 of the rotational bearing. The ring 90 defines a central opening 92 concentric with axis 46 (see FIG. 4). Resilient tapered gripping members 94 extend inward into the opening 92 for gripping the tip 24 of the dental curing device 20. The ring 90 includes a pair of annular flanges 96 projecting in a generally radial direction outward from the ring. The flanges 96 are spaced apart to define an annular groove 98 between the flanges for receiving the inner race 44 of the bearing 40. Desirably, the ring 90 and gripping members 94 are integrally formed (e.g., molded) as a one-piece structure of resilient material. The ring 90 is sized for a snap fit of the inner race 44 of the bearing 40 inside the groove 98. By way of example but not limitation, the ring 90 and gripping members 94 may be formed from 70-durometer rubber, which is rigid enough for securely holding the device 10 on the tip 24 of the curing device 20 but not so rigid that the tip cannot be easily snap-fit inside the rotational bearing 40. Further, the resilient nature of the retaining device 50 allows it to accommodate light tips 24 (or other curing device components) having substantially different diameters falling within a relatively wide range of sizes. The retaining device 50 may have other shapes without departing from the scope of this invention.

Referring to FIGS. 4 and 5, the counterweight 60 comprises a curved counterweight member 100 immovably affixed (e.g., adhered) to face 68 of the lower section 32B of the support member 32 and to the lower surface of the outer component 42 of the rotational bearing 40. The counterweight 60 is of a suitably heavy material, such as a tungsten alloy, a very dense yet non-toxic metal which minimizes the size of the counterweight. By way of example, the alloy may have a density in excess of 18 $g/cm^3$. Desirably, the counterweight member 100 has a curved generally part-circular upper surface 102 that wraps around and closely conforms in size and shape to the curved lower surface of the outer annular 44 race of the rotational bearing 40. (The outer race 44 is adhered to this surface 102.) The counterweight member 100 also has upward-facing end surfaces 104 that desirably seats against and are immovably affixed (e.g., adhered) to downward-facing end surfaces 106 of the bearing mount 36. The lower surface 110 of the counterweight member 100 tapers in a direction away from the support 32 to facilitate partial entry into the mouth of a patient, as needed or desired.

The counterweight 60 may have other shapes and be placed at other locations on the support member 32 without departing from the scope of this invention. Further, while the illustrated counterweight comprises only one member, the counterweight can include two or more separate members.

The overall weight of the counterweight 60 is sufficient to offset the weight of the filter member 30 and maintain it upright as the tip 24 is turned and/or when the body 22 of the curing device 20 is rotated into position. By way of example, this weight may be in the range of 5-40 grams, and even more particularly in the range of 15-25 grams. Desirably, the counterweight 60 is positioned close enough to the rotational bearing 40 to prevent rocking as the filter member 30 approaches a resting position as determined by the counterweight. In the illustrated embodiment, the counterweight 60 is located immediately adjacent the rotational bearing 40, with the counterweight and rotational bearing spaced apart a distance no greater than 0-0.125 in. This location reduces the overall size of the light filtering device 10 for maximum compactness and also minimizes any pendulum-like rocking of the filter member 30 when the tip 24 or curing device 20 is rotated or repositioned by the care provider. However, the counterweight 60 can be located more remotely from the rotational bearing 40 without departing from the scope of this invention.

The components of the light filtering device 10 described above may be adhesively bonded together using a DP 190 epoxy available from 3M Company. It is clear for good esthetics, has a very high bond strength at room temperature, and is not brittle (making it flex slightly if the device is dropped to avoid breaking the adhesive bond).

Figure 2:
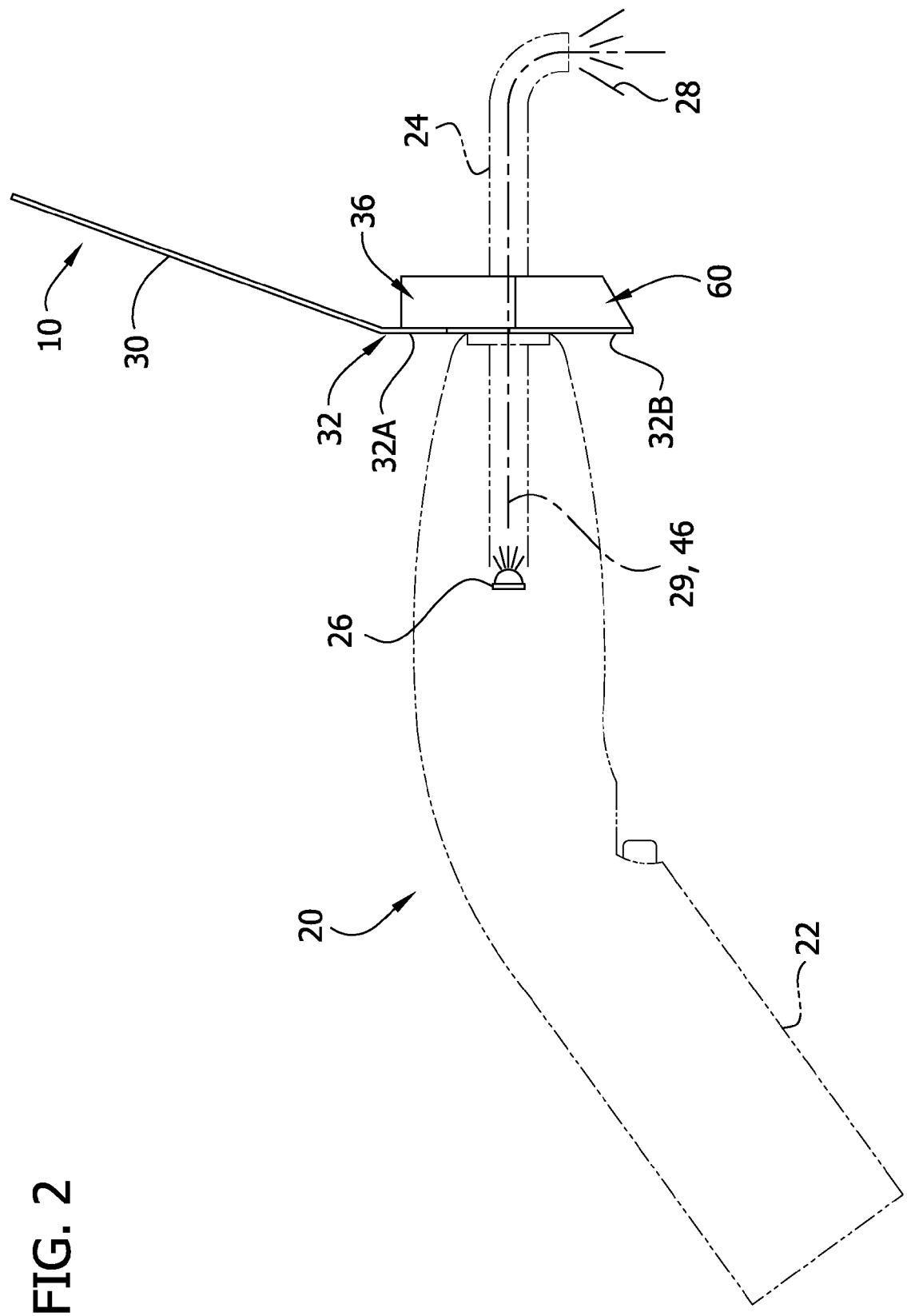
FIG. 2 is a side elevation of the light filtering device of FIG. 1 mounted on the tip of a dental curing device.

In use, the light filtering device 10 is installed on the tip 24 of the curing device, as illustrated in FIG. 2. As thus installed, the retaining device 50 grips the tip 24 and holds it substantially concentric with the axis of rotation 46 and rotationally stationary relative to the inner component 44 of the rotational bearing 40. Thus, when the care provider rotates the tip 24 of the curing device 20 and/or rotates or repositions the curing device itself during a procedure, the retaining device 50 and the inner component 44 of the rotational bearing 40 will rotate with the tip relative to the outer component 42 of the rotational bearing immovably offered to the support 32. The counterweight 60 functions to keep the filter member 30 upright and in proper position during the procedure to block curing light 28 emitted from the light-emitting device 26, regardless of how the tip 24 is turned, the patient is turned or tilted, or how the curing device is rotated. In effect, the light filtering device 10 "self-positions" during the procedure to remain in the proper upright orientation, without the need for any adjustment or repositioning by the care provider or other person.

It will be observed that the primary movement of the body 22 and tip 24 of the curing device 20 is rotational as the clinician determines the correct position. Sometimes during use the body 22 of the curing device 20 may be rotated one way and the tip 24 grasped and rotated in an opposite direction to reach the desired spot in a patient's mouth. Having a filter member 30 that maintains its upright position during these movements creates operational efficiency. In view of the rotational movements of the body and light tip of the curing device, the rotational bearing 40 positioned in the plane of these movements facilitates auto-positioning of the device. This arrangement also allows the light tip to protrude through the inside of the bearing.

As noted above, a light filtering device 10 of this invention permits operational efficiencies. By way of example, a clinician curing a composite resin does not need to hold the curing device 20 with one hand and rotate the filter member 30 with the other to achieve the correct position; one hand is adequate. Also, if the position of the filter member 30 needs to be rotated slightly, it is easily done with a nudge with either hand. The body 22 of the curing device 20 does not need to be grasped tightly to rotate the filter member 30. Still further, using the light filtering device 10, only one individual is needed to cure the composite.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions without departing from the scope of the invention, it is intended that all matter contained in the above description and shown in the accompanying drawing[s] shall be interpreted as illustrative and not in a limiting sense.

What is claimed is:

1. A self-positioning dental light filtering device, comprising
    a transparent filter member for blocking optically harmful light emitted from a tip of a dental curing device,
    a support for supporting the filter member in an upright position above the tip of the curing device,
    a rotational bearing having concentric outer and inner components rotatable relative to one another about an axis of rotation, the outer component being immovable relative to the support and the inner component defining an opening for receiving the tip or other component of the dental curing device,
    a retaining device for holding the tip or other component of the dental curing device substantially centered inside the rotational bearing and substantially rotationally stationary relative to the inner component of the rotational bearing when the tip or other component is received in the opening, and
    a counterweight below the rotational bearing for causing the filter member to remain in said upright position when the tip of the curing device and/or curing device itself is rotated about said axis of rotation.

2. The light filtering device of claim 1, wherein the support lies in a first plane generally perpendicular to the axis of rotation, and wherein the filter member lies in a second plane extending at an angle of plus or minus 0-60 degrees relative to the first plane.

3. The light filtering device of claim 1, wherein the rotational bearing is a thin-section rolling-element bearing.

4. The light filtering device of claim 1, further comprising a bearing mount immovably affixed to the support, and wherein the outer component of the rotational bearing is immovably affixed to the bearing mount.

5. The light filtering device of claim 4, wherein said bearing mount comprises a member positioned immediately above the rotational bearing and having a curved lower surface closely conforming to the curvature of the outer component of the rotational bearing.

6. The light filtering device of claim 4, wherein the support has an upper section disposed above the rotational bearing and a lower section disposed below the rotational bearing, wherein the bearing mount is affixed to the upper section, and wherein the counterweight is affixed to the lower section.

7. The light filtering device of claim 6, wherein the counterweight is immovably affixed to the lower section of the support immediately adjacent the rotational bearing.

8. The light filtering device of claim 7, wherein said counterweight comprises a curved member positioned immediately below the rotational bearing and having a curvature substantially identical to a curvature of the outer component of the rotational bearing.

9. The light filtering device of claim 7, wherein the counterweight is also immovably affixed to the bearing mount.

10. The light filtering device of claim 1, wherein the counterweight is immovably affixed to the support immediately adjacent the rotational bearing.

11. The light filtering device of claim 10, wherein said counterweight comprises a curved member positioned immediately below the rotational bearing and having a curvature substantially identical to a curvature of the outer component of the rotational bearing.

12. The light filtering device of claim 1, wherein the support and the filter member are integrally formed as one-piece from the same material.

13. The light filtering device of claim 1, wherein the retaining device comprises an annular retaining member secured to the inner component of the rotational bearing and configured for gripping the tip of the dental curing device.

14. The light filtering device of claim 1, wherein the retaining device is configured for holding the tip or other component of the dental curing device generally concentric with said axis of rotation.

15. The light filtering device of claim 14, wherein said retaining device comprises a ring fitted inside said opening, and resilient gripping members extending inward into the opening for gripping the tip or other component of the dental curing device.

16. The light filtering device of claim 1, wherein the transparent filter member is of a color, tint or material capable of mitigating the harmful visual effects of the dental curing light.

17. The light filtering device of claim 1, wherein the counterweight is positioned close enough to the rotational bearing to prevent rocking as the filter member approaches a resting position as determined by the counterweight.

* * * * *